United States Patent
Devauchelle et al.

(12)

(10) Patent No.: US 6,169,172 B1
(45) Date of Patent: Jan. 2, 2001

(54) USE OF A PROLACTIN RECEPTOR OR GROWTH HORMONE RECEPTOR INTRACYTOPLASMIC DOMAIN FOR ACHIEVING PROTEIN SECRETION

(75) Inventors: Gérard Devauchelle, Saint-Christol-lez-Alès; Laurence Garnier, Norières-les-Avignon; Claire Cahoreau, Montpellier; Martine Cerutti, Saint-Christol-lez-Alès, all of (FR)

(73) Assignees: Institut National de la Recherche Agronomique (Inra); Centre National de la Recherche Scientifique (Cnrs), both of Paris (FR)

( * ) Notice: Under 35 U.S.C. 154(b), the term of this patent shall be extended for 0 days.

(21) Appl. No.: 09/000,145
(22) PCT Filed: Aug. 2, 1996
(86) PCT No.: PCT/FR96/01237
  § 371 Date: Mar. 16, 1998
  § 102(e) Date: Mar. 16, 1998

(87) PCT Pub. No.: WO97/05259
  PCT Pub. Date: Feb. 13, 1997

(30) Foreign Application Priority Data
  Aug. 2, 1995 (FR) .................................... 95 09420

(51) Int. Cl.$^7$ .......................... C07H 21/04; C12N 15/11; C12N 15/62
(52) U.S. Cl. ...................... 536/23.4; 536/23.1; 435/69.1; 435/172.3; 530/350
(58) Field of Search ................ 435/69.1, 172.3; 530/350; 536/23.1, 23.4, 23.5

*Primary Examiner*—Gary L. Kunz
*Assistant Examiner*—Nirmal S. Basi
(74) *Attorney, Agent, or Firm*—Oblon, Spivak, McClelland, Maier & Neustadt, P.C.

(57) ABSTRACT

The use of a prolactin receptor intracytoplasmic domain or a growth hormone receptor intracytoplasmic domain, or of a fragment of either one of said domains, for achieving the secretion of a protein of interest produced in a eukaryotic host cell, is disclosed.

13 Claims, 2 Drawing Sheets

SEQUENCE LISTING

<160> NUMBER OF SEQ ID NOS: 6

<210> SEQ ID NO 1
<211> LENGTH: 620
<212> TYPE: PRT
<213> ORGANISM: Homo sapiens

<400> SEQUENCE: 1

```
Phe Ser Gly Ser Glu Ala Thr Ala Ala Ile Leu Ser Arg Ala Pro Trp
 1               5                  10                  15

Ser Leu Gln Ser Val Asn Pro Gly Leu Lys Thr Asn Ser Ser Lys Glu
            20                  25                  30

Pro Lys Phe Thr Lys Cys Arg Ser Pro Glu Arg Glu Thr Phe Ser Cys
        35                  40                  45

His Trp Thr Asp Glu Val His His Gly Thr Lys Asn Leu Gly Pro Ile
    50                  55                  60

Gln Leu Phe Tyr Thr Arg Arg Asn Thr Gln Glu Trp Thr Gln Glu Trp
65                  70                  75                  80

Lys Glu Cys Pro Asp Tyr Val Ser Ala Gly Glu Asn Ser Cys Tyr Phe
                85                  90                  95

Asn Ser Ser Phe Thr Ser Ile Trp Ile Pro Tyr Cys Ile Lys Leu Thr
            100                 105                 110

Ser Asn Gly Gly Thr Val Asp Glu Lys Cys Phe Ser Val Asp Glu Ile
        115                 120                 125

Val Gln Pro Asp Pro Pro Ile Ala Leu Asn Trp Thr Leu Leu Asn Val
    130                 135                 140

Ser Leu Thr Gly Ile His Ala Asp Ile Gln Val Arg Trp Glu Ala Pro
145                 150                 155                 160

Arg Asn Ala Asp Ile Gln Lys Gly Trp Met Val Leu Glu Tyr Glu Leu
                165                 170                 175

Gln Tyr Lys Glu Val Asn Glu Thr Lys Trp Lys Met Met Asp Pro Ile
            180                 185                 190

Leu Thr Thr Ser Val Pro Val Tyr Ser Leu Lys Val Asp Lys Glu Tyr
        195                 200                 205
```

-continued

```
Glu Val Arg Val Arg Ser Lys Gln Arg Asn Ser Gly Asn Tyr Gly Glu
    210                 215                 220
Phe Ser Glu Val Leu Tyr Val Thr Leu Pro Gln Met Ser Gln Phe Thr
225                 230                 235                 240
Cys Glu Glu Asp Phe Tyr Phe Pro Trp Leu Leu Ile Ile Ile Phe Gly
                245                 250                 255
Ile Phe Gly Leu Thr Val Met Leu Phe Val Phe Leu Phe Ser Lys Gln
            260                 265                 270
Gln Arg Ile Lys Met Leu Ile Leu Pro Pro Val Pro Val Pro Lys Ile
        275                 280                 285
Lys Gly Ile Asp Pro Asp Leu Leu Lys Glu Gly Lys Leu Glu Glu Val
    290                 295                 300
Asn Thr Ile Leu Ala Ile His Asp Ser Tyr Lys Pro Glu Phe His Ser
305                 310                 315                 320
Asp Asp Ser Trp Val Glu Phe Ile Glu Leu Asp Ile Asp Glu Pro Asp
                325                 330                 335
Glu Lys Thr Glu Glu Ser Asp Thr Asp Arg Leu Leu Ser Ser Asp His
            340                 345                 350
Glu Lys Ser His Ser Asn Leu Gly Val Lys Asp Gly Asp Ser Gly Arg
        355                 360                 365
Thr Ser Cys Cys Glu Pro Asp Ile Leu Glu Thr Asp Phe Asn Ala Asn
    370                 375                 380
Asp Ile His Glu Gly Thr Ser Glu Val Ala Gln Pro Gln Arg Leu Lys
385                 390                 395                 400
Gly Glu Ala Asp Leu Leu Cys Leu Asp Gln Lys Asn Gln Asn Asn Ser
                405                 410                 415
Pro Tyr His Asp Ala Cys Pro Ala Thr Gln Gln Pro Ser Val Ile Gln
            420                 425                 430
Ala Glu Lys Asn Lys Pro Gln Pro Leu Pro Thr Glu Gly Ala Glu Ser
        435                 440                 445
Thr His Gln Ala Ala His Ile Gln Leu Ser Asn Pro Ser Ser Leu Ser
    450                 455                 460
Asn Ile Asp Phe Tyr Ala Gln Val Ser Asp Ile Thr Pro Ala Gly Ser
465                 470                 475                 480
Val Val Leu Ser Pro Gly Gln Lys Asn Lys Ala Gly Met Ser Gln Cys
                485                 490                 495
Asp Met His Pro Glu Met Val Ser Leu Cys Gln Glu Asn Phe Leu Met
            500                 505                 510
Asp Asn Ala Tyr Phe Cys Glu Ala Asp Ala Lys Lys Cys Leu Pro Val
        515                 520                 525
Ala Pro His Ile Lys Val Glu Ser His Ile Gln Pro Ser Leu Asn Gln
    530                 535                 540
Glu Asp Ile Tyr Ile Thr Thr Glu Ser Leu Thr Thr Ala Ala Gly Arg
545                 550                 555                 560
Pro Gly Thr Gly Glu His Val Pro Gly Ser Glu Met Pro Val Pro Asp
                565                 570                 575
Tyr Thr Ser Ile His Ile Val Gln Ser Pro Gln Gly Leu Ile Leu Asn
            580                 585                 590
Ala Thr Ala Leu Pro Leu Pro Asp Lys Glu Phe Leu Ser Ser Cys Gly
        595                 600                 605
Tyr Val Ser Thr Asp Gln Leu Asn Lys Ile Met Pro
    610                 615                 620
```

```
<210> SEQ ID NO 2
<211> LENGTH: 599
<212> TYPE: PRT
<213> ORGANISM: Homo sapiens

<400> SEQUENCE: 2

Gly Gln Leu Pro Pro Gly Lys Pro Glu Ile Phe Lys Cys Arg Ser Pro
 1               5                  10                  15

Asn Lys Glu Thr Phe Thr Cys Trp Trp Arg Pro Gly Thr Asp Gly Gly
             20                  25                  30

Leu Pro Thr Asn Tyr Ser Leu Thr Tyr His Arg Glu Gly Glu Thr Leu
         35                  40                  45

Met His Glu Cys Pro Asp Tyr Ile Thr Gly Gly Pro Asn Ser Cys His
     50                  55                  60

Phe Gly Lys Gln Tyr Thr Ser Met Trp Arg Thr Tyr Ile Met Met Val
 65                  70                  75                  80

Asn Ala Thr Asn Gln Met Gly Ser Ser Phe Ser Asp Glu Leu Tyr Val
                 85                  90                  95

Asp Val Thr Tyr Ile Val Gln Pro Asp Pro Pro Leu Glu Leu Ala Val
            100                 105                 110

Glu Val Lys Gln Pro Glu Asp Arg Lys Pro Tyr Leu Trp Ile Lys Trp
        115                 120                 125

Ser Pro Pro Thr Leu Ile Asp Leu Lys Thr Gly Trp Phe Thr Leu Leu
    130                 135                 140

Tyr Glu Ile Arg Leu Lys Pro Glu Lys Ala Ala Glu Trp Glu Ile His
145                 150                 155                 160

Phe Ala Gly Gln Gln Thr Glu Phe Lys Ile Leu Ser Leu His Pro Gly
                165                 170                 175

Gln Lys Tyr Leu Val Gln Val Arg Cys Lys Pro Asp His Gly Tyr Trp
            180                 185                 190

Ser Ala Trp Ser Pro Ala Thr Phe Ile Gln Ile Pro Ser Asp Phe Thr
        195                 200                 205

Met Asn Asp Thr Thr Val Trp Ile Ser Val Ala Val Leu Ser Ala Val
    210                 215                 220

Ile Cys Leu Ile Ile Val Trp Ala Val Ala Leu Lys Gly Tyr Ser Met
225                 230                 235                 240

Val Thr Cys Ile Phe Pro Pro Val Pro Gly Pro Lys Ile Lys Gly Phe
                245                 250                 255

Asp Ala His Leu Leu Glu Lys Gly Lys Ser Glu Glu Leu Leu Ser Ala
            260                 265                 270

Leu Gly Cys Gln Asp Phe Pro Pro Thr Ser Asp Tyr Glu Asp Leu Leu
        275                 280                 285

Val Glu Tyr Leu Glu Val Asp Asp Ser Glu Asp Gln His Leu Met Ser
    290                 295                 300

Val His Ser Lys Glu His Pro Ser Gln Gly Met Lys Pro Thr Tyr Leu
305                 310                 315                 320

Asp Pro Asp Thr Asp Ser Gly Arg Gly Ser Cys Asp Ser Pro Ser Leu
                325                 330                 335

Leu Ser Glu Lys Cys Glu Glu Pro Gln Ala Asn Pro Ser Thr Phe Tyr
            340                 345                 350

Asp Pro Glu Val Ile Glu Lys Pro Glu Asn Pro Glu Thr Thr His Thr
        355                 360                 365

Trp Asp Pro Gln Cys Ile Ser Met Glu Gly Lys Ile Pro Tyr Phe His
    370                 375                 380
```

-continued

Ala Gly Gly Ser Lys Cys Ser Thr Trp Pro Leu Pro Gln Pro Ser Gln
385                 390                 395                 400

His Asn Pro Arg Ser Ser Tyr His Asn Ile Thr Asp Val Cys Glu Leu
            405                 410                 415

Ala Val Gly Pro Ala Gly Ala Pro Ala Thr Leu Leu Asn Glu Ala Gly
        420                 425                 430

Lys Asp Ala Leu Lys Ser Ser Gln Thr Ile Lys Ser Arg Glu Glu Gly
            435                 440                 445

Lys Ala Thr Gln Gln Arg Glu Val Glu Ser Phe His Ser Glu Thr Asp
450                 455                 460

Gln Asp Thr Pro Trp Leu Leu Pro Gln Glu Lys Thr Pro Phe Gly Ser
465                 470                 475                 480

Ala Lys Pro Leu Asp Tyr Val Glu Ile His Lys Val Asn Lys Asp Gly
                485                 490                 495

Ala Leu Ser Leu Leu Pro Lys Gln Arg Glu Asn Ser Gly Lys Pro Lys
            500                 505                 510

Lys Pro Gly Thr Pro Glu Asn Asn Lys Glu Tyr Ala Lys Val Ser Gly
            515                 520                 525

Val Met Asp Asn Asn Ile Leu Val Leu Val Pro Asp Pro His Ala Lys
530                 535                 540

Asn Val Ala Cys Phe Glu Glu Ser Ala Lys Glu Ala Pro Pro Ser Leu
545                 550                 555                 560

Glu Gln Asn Gln Ala Glu Lys Ala Leu Ala Asn Phe Thr Ala Thr Ser
                565                 570                 575

Ser Lys Cys Arg Leu Gln Leu Gly Gly Leu Asp Tyr Leu Asp Pro Ala
            580                 585                 590

Cys Phe Thr His Ser Phe His
            595

<210> SEQ ID NO 3
<211> LENGTH: 620
<212> TYPE: PRT
<213> ORGANISM: Oryctolagus cuniculus

<400> SEQUENCE: 3

Phe Ser Gly Ser Glu Ala Thr Pro Ala Thr Leu Gly Arg Ala Ser Glu
 1               5                   10                  15

Ser Val Gln Arg Val His Pro Gly Leu Gly Thr Asn Ser Ser Gly Lys
                20                  25                  30

Pro Lys Phe Thr Lys Cys Arg Ser Pro Glu Leu Glu Thr Phe Ser Cys
            35                  40                  45

His Trp Thr Asp Gly Val His His Gly Leu Lys Ser Pro Gly Ser Val
     50                  55                  60

Gln Leu Phe Tyr Ile Arg Arg Asn Thr Gln Glu Trp Thr Gln Glu Trp
 65                  70                  75                  80

Lys Glu Cys Pro Asp Tyr Val Ser Ala Gly Glu Asn Ser Cys Tyr Phe
                85                  90                  95

Asn Ser Ser Tyr Thr Ser Ile Trp Ile Pro Tyr Cys Ile Lys Leu Thr
            100                 105                 110

Asn Asn Gly Gly Met Val Asp Gln Lys Cys Phe Ser Val Glu Glu Ile
            115                 120                 125

Val Gln Pro Asp Pro Pro Ile Gly Leu Asn Trp Thr Leu Leu Asn Val
        130                 135                 140

Ser Leu Thr Gly Ile His Ala Asp Ile Gln Val Arg Trp Glu Pro Pro

-continued

```
            145                 150                 155                 160
    Pro Asn Ala Asp Val Gln Lys Gly Trp Ile Val Leu Glu Tyr Glu Leu
                    165                 170                 175
    Gln Tyr Lys Glu Val Asn Glu Thr Gln Trp Lys Met Met Asp Pro Val
                    180                 185                 190
    Leu Ser Thr Ser Val Pro Val Tyr Ser Leu Arg Leu Asp Lys Glu Tyr
                    195                 200                 205
    Glu Val Arg Val Arg Ser Arg Gln Arg Ser Ser Glu Lys Tyr Gly Glu
                    210                 215                 220
    Phe Ser Glu Val Leu Tyr Val Thr Leu Pro Gln Met Ser Pro Phe Thr
    225                 230                 235                 240
    Cys Glu Glu Asp Phe Arg Phe Pro Trp Phe Leu Ile Ile Ile Phe Gly
                    245                 250                 255
    Ile Phe Gly Leu Thr Val Met Leu Phe Val Phe Ile Phe Ser Lys Gln
                    260                 265                 270
    Gln Arg Ile Lys Met Leu Ile Leu Pro Pro Val Pro Val Pro Lys Ile
                    275                 280                 285
    Lys Gly Ile Asp Pro Asp Leu Leu Lys Glu Gly Lys Leu Glu Glu Val
                    290                 295                 300
    Asn Thr Ile Leu Ala Ile Gln Asp Ser Tyr Lys Pro Glu Phe Tyr Asn
    305                 310                 315                 320
    Asp Asp Ser Trp Val Glu Phe Ile Glu Leu Asp Ile Asp Pro Asp
                    325                 330                 335
    Glu Lys Thr Glu Gly Ser Asp Thr Asp Arg Leu Leu Ser Asn Ser His
                    340                 345                 350
    Gln Lys Ser Leu Ser Val Leu Ala Ala Lys Asp Asp Ser Gly Arg
                    355                 360                 365
    Thr Ser Cys Tyr Glu Pro Asp Ile Leu Glu Asn Asp Phe Asn Ala Ser
                    370                 375                 380
    Asp Gly Cys Asp Gly Asn Ser Glu Val Ala Gln Pro Gln Arg Leu Lys
    385                 390                 395                 400
    Gly Glu Ala Asp Leu Leu Cys Leu Asp Gln Lys Asn Gln Asn Asn Ser
                    405                 410                 415
    Pro Tyr His Asp Val Ser Pro Ala Ala Gln Gln Pro Glu Val Val Leu
                    420                 425                 430
    Ala Glu Glu Asp Lys Pro Arg Pro Leu Leu Thr Gly Glu Ile Glu Ser
                    435                 440                 445
    Thr Leu Gln Ala Ala Pro Ser Gln Leu Ser Asn Pro Asn Ser Leu Ala
                    450                 455                 460
    Asn Ile Asp Phe Tyr Ala Gln Val Ser Asp Ile Thr Pro Ala Gly Ser
    465                 470                 475                 480
    Val Val Leu Ser Pro Gly Gln Lys Asn Lys Ala Gly Asn Ser Gln Cys
                    485                 490                 495
    Asp Ala His Pro Glu Val Val Ser Leu Cys Gln Thr Asn Phe Ile Met
                    500                 505                 510
    Asp Asn Ala Tyr Phe Cys Glu Ala Asp Ala Lys Lys Cys Ile Ala Val
                    515                 520                 525
    Ala Pro His Val Asp Val Glu Ser Arg Val Glu Pro Ser Phe Asn Gln
                    530                 535                 540
    Glu Asp Ile Tyr Ile Thr Thr Glu Ser Leu Thr Thr Ala Glu Arg
    545                 550                 555                 560
    Ser Gly Thr Ala Glu Asp Ala Pro Gly Ser Glu Met Pro Val Pro Asp
                    565                 570                 575
```

-continued

Tyr Thr Ser Ile His Leu Val Gln Ser Pro Gln Gly Leu Val Leu Asn
            580                 585                 590

Ala Ala Thr Leu Pro Leu Pro Asp Lys Glu Phe Leu Ser Ser Cys Gly
            595                 600                 605

Tyr Val Ser Thr Asp Gln Leu Asn Lys Ile Leu Pro
            610                 615                 620

<210> SEQ ID NO 4
<211> LENGTH: 593
<212> TYPE: PRT
<213> ORGANISM: Oryctolagus cuniculus

<400> SEQUENCE: 4

Gly Gln Ser Pro Pro Gly Lys Pro Phe Ile Phe Lys Cys Arg Ser Pro
  1               5                  10                  15

Glu Lys Glu Thr Phe Thr Cys Trp Trp Arg Pro Gly Ala Asp Gly Gly
                 20                  25                  30

Leu Pro Thr Asn Tyr Thr Leu Thr Tyr His Lys Glu Gly Glu Thr Ile
             35                  40                  45

Thr His Glu Cys Pro Asp Tyr Lys Thr Gly Gly Pro Asn Ser Cys Tyr
         50                  55                  60

Phe Ser Lys Lys His Thr Ser Ile Trp Thr Ile Tyr Ile Ile Thr Val
 65                  70                  75                  80

Asn Ala Thr Asn Gln Met Gly Ser Ser Val Ser Asp Pro Arg Tyr Val
                 85                  90                  95

Asp Val Thr Tyr Ile Val Glu Pro Asp Pro Pro Val Asn Leu Thr Leu
                100                 105                 110

Glu Val Lys His Pro Glu Asp Arg Lys Pro Tyr Leu Trp Val Lys Trp
            115                 120                 125

Leu Pro Pro Thr Leu Val Asp Val Arg Ser Gly Trp Leu Thr Leu Gln
        130                 135                 140

Tyr Glu Ile Arg Leu Lys Pro Glu Lys Ala Ala Glu Trp Glu Thr His
145                 150                 155                 160

Phe Ala Gly Gln Gln Thr Gln Phe Lys Ile Leu Ser Leu Tyr Pro Gly
                165                 170                 175

Gln Lys Tyr Leu Val Gln Val Arg Cys Lys Pro Asp His Gly Phe Trp
            180                 185                 190

Ser Val Trp Ser Pro Glu Ser Ser Ile Gln Ile Pro Asn Asp Phe Thr
        195                 200                 205

Met Lys Asp Ile Thr Val Trp Ile Phe Val Ala Val Leu Ser Thr Ile
    210                 215                 220

Ile Cys Leu Ile Met Val Trp Ala Val Ala Leu Lys Gly Tyr Ser Met
225                 230                 235                 240

Val Thr Cys Ile Phe Pro Pro Val Pro Gly Pro Lys Ile Lys Gly Phe
                245                 250                 255

Asp Thr His Leu Leu Glu Lys Gly Lys Ser Glu Glu Leu Leu Ser Ala
            260                 265                 270

Phe Gly Cys Gln Asp Phe Pro Pro Thr Ala Asp Cys Glu Asp Leu Leu
        275                 280                 285

Val Glu Phe Leu Glu Val Asp Asp Ser Glu Asp Gln Gln Leu Met Pro
    290                 295                 300

Ala His Ser Lys Glu His Ser Gly Pro Gly Met Lys Pro Thr Asp Leu
305                 310                 315                 320

Asp Pro Asp Asn Asp Ser Gly Arg Gly Ser Cys Asp Ser Pro Ser Leu

-continued

```
                    325                 330                 335
Leu Ser Glu Lys Cys Glu Pro Gln Ala Asn Pro Ser Thr Phe His
                340                 345                 350
Thr Pro Glu Val Ile Glu Gln Pro Glu Lys Pro Lys Ala Asn Val Thr
                355                 360                 365
His Thr Trp Asp Pro Gln Thr Ile Ser Leu Val Gly Lys Met Pro Tyr
                370                 375                 380
Leu Ser Val Asn Gly Ser Lys Ser Ser Thr Trp Pro Leu Leu Gln Pro
385                 390                 395                 400
Gly Gln His Asn Thr Asn Ser Pro Tyr His Asn Ile Ala Asp Met Cys
                405                 410                 415
Lys Leu Ala Thr Ser Leu Asp Lys Ile Asp Lys Asp Ala Leu Gln Ser
                420                 425                 430
Ser Lys Thr Thr Glu Ala Ala Gly Glu Glu Lys Ala Thr Lys Gln Arg
                435                 440                 445
Glu Val Glu Ser Ser His Ser Lys Ala Glu Gln Asp Thr Gly Trp Leu
                450                 455                 460
Leu Pro Lys Glu Lys Pro Pro Phe Ile Ser Pro Lys Pro Leu Asp Tyr
465                 470                 475                 480
Val Glu Ile His Lys Val Asn Lys Asp Gly Ala Leu Ser Leu Leu Leu
                485                 490                 495
Lys Gln Lys Glu Asn Gly Asp Gln Thr Gly Lys Ala Gly Thr Pro Glu
                500                 505                 510
Thr Ser Lys Glu Tyr Ala Lys Val Ser Arg Val Met Asp Asn Asn Ile
                515                 520                 525
Leu Val Leu Val Gln Asp Pro Gly Ala Gln Asn Val Ala Leu Phe Glu
                530                 535                 540
Glu Ser Thr Lys Glu Ala Pro Pro Ser Pro Ser Gln Asn Gln Ala Glu
545                 550                 555                 560
Lys Asp Leu Ser Ser Phe Ser Thr Ala Pro Ser Asp Cys Arg Leu Gln
                565                 570                 575
Gln Gly Gly Leu Asp Tyr Leu Asp Pro Ala Cys Phe Met His Ser Leu
                580                 585                 590
His

<210> SEQ ID NO 5
<211> LENGTH: 620
<212> TYPE: PRT
<213> ORGANISM: Rattus rattus

<400> SEQUENCE: 5

Phe Pro Gly Ser Gly Ala Thr Pro Ala Thr Leu Gly Lys Ala Ser Pro
  1               5                  10                  15
Val Leu Gln Arg Ile Asn Pro Ser Leu Arg Glu Ser Ser Ser Gly Lys
                 20                  25                  30
Pro Arg Phe Thr Lys Cys Arg Ser Pro Glu Leu Glu Thr Phe Ser Cys
             35                  40                  45
Tyr Trp Thr Glu Gly Asp Asp His Asn Leu Lys Val Pro Gly Ser Ile
         50                  55                  60
Gln Leu Tyr Tyr Ala Arg Arg Ile Ala His Glu Trp Thr Pro Glu Trp
 65                  70                  75                  80
Lys Glu Cys Pro Asp Tyr Val Ser Ala Gly Ala Asn Ser Cys Tyr Phe
                 85                  90                  95
Asn Ser Ser Tyr Thr Ser Ile Trp Ile Pro Tyr Cys Ile Lys Leu Thr
```

-continued

```
                100             105             110
Thr Asn Gly Asp Leu Leu Asp Glu Lys Cys Phe Thr Val Asp Glu Ile
            115             120             125
Val Gln Pro Asp Pro Pro Ile Gly Leu Asn Trp Thr Leu Leu Asn Ile
            130             135             140
Ser Leu Pro Gly Ile Arg Gly Asp Ile Gln Val Ser Trp Gln Pro Pro
145             150             155             160
Pro Ser Ala Asp Val Leu Lys Gly Trp Ile Ile Leu Glu Tyr Glu Ile
            165             170             175
Gln Tyr Lys Glu Val Asn Glu Thr Lys Trp Lys Thr Met Ser Pro Ile
            180             185             190
Trp Ser Thr Ser Val Pro Leu Tyr Ser Leu Arg Leu Asp Lys Glu His
            195             200             205
Glu Val Arg Val Arg Ser Arg Gln Arg Ser Phe Glu Lys Tyr Ser Glu
            210             215             220
Phe Ser Glu Val Leu Arg Val Thr Phe Pro Gln Met Asp Thr Leu Ala
225             230             235             240
Ala Cys Glu Glu Asp Phe Arg Phe Pro Trp Phe Leu Ile Ile Ile Phe
            245             250             255
Gly Ile Phe Gly Val Ala Val Met Leu Phe Val Val Ile Phe Ser Lys
            260             265             270
Gln Gln Arg Ile Lys Met Leu Ile Leu Pro Pro Val Pro Val Pro Lys
            275             280             285
Ile Lys Gly Ile Asp Pro Asp Leu Leu Lys Glu Gly Lys Leu Glu Glu
            290             295             300
Val Asn Thr Ile Leu Gly Ile His Asp Asn Tyr Lys Pro Asp Phe Tyr
305             310             315             320
Asn Asp Asp Ser Trp Val Glu Phe Ile Glu Leu Asp Ile Asp Asp Ala
            325             330             335
Asp Glu Lys Thr Glu Glu Ser Asp Thr Asp Arg Leu Leu Ser Asp Asp
            340             345             350
Gln Glu Lys Ser Ala Gly Ile Leu Gly Ala Lys Asp Asp Asp Ser Gly
            355             360             365
Arg Thr Ser Cys Tyr Asp Pro Asp Ile Leu Asp Thr Asp Phe His Thr
            370             375             380
Ser Asp Met Cys Asp Gly Thr Ser Glu Phe Ala Gln Pro Gln Lys Leu
385             390             395             400
Lys Ala Glu Ala Asp Leu Leu Cys Leu Asp Gln Lys Asn Leu Lys Asn
            405             410             415
Ser Pro Tyr Asp Ala Ser Leu Gly Ser Leu His Pro Ser Ile Thr Leu
            420             425             430
Thr Met Glu Asp Lys Pro Gln Pro Leu Leu Gly Ser Glu Thr Glu Ser
            435             440             445
Thr His Gln Leu Pro Ser Thr Pro Met Ser Ser Pro Val Ser Leu Ala
            450             455             460
Asn Ile Asp Phe Tyr Ala Gln Val Ser Asp Ile Thr Pro Ala Gly Gly
465             470             475             480
Val Val Leu Ser Pro Gly Gln Lys Ile Lys Ala Gly Leu Ala Gln Gly
            485             490             495
Asn Thr Gln Leu Glu Val Ala Ala Pro Cys Gln Glu Asn Tyr Ser Met
            500             505             510
Asn Ser Ala Tyr Phe Cys Glu Ser Asp Ala Lys Lys Cys Ile Ala Ala
            515             520             525
```

```
Ala Pro His Met Glu Ala Thr Thr Cys Val Lys Pro Ser Phe Asn Gln
    530                 535                 540

Glu Asp Ile Tyr Ile Thr Thr Glu Ser Leu Thr Thr Ala Arg Met
545                 550                 555                 560

Ser Glu Thr Ala Asp Thr Ala Pro Asp Ala Glu Pro Val Pro Asp Tyr
                565                 570                 575

Thr Thr Val His Thr Val Lys Ser Pro Arg Gly Leu Ile Leu Asn Ala
            580                 585                 590

Thr Ala Leu Pro Leu Pro Asp Lys Lys Phe Leu Ser Ser Cys Gly
            595                 600                 605

Tyr Val Ser Thr Asp Gln Leu Asn Lys Ile Met Gln
    610                 615                 620

<210> SEQ ID NO 6
<211> LENGTH: 592
<212> TYPE: PRT
<213> ORGANISM: Rattus rattus

<400> SEQUENCE: 6

Gly Gln Ser Pro Pro Gly Lys Pro Glu Ile His Lys Cys Arg Ser Pro
1               5                   10                  15

Asp Lys Glu Thr Phe Thr Cys Trp Trp Asn Pro Gly Thr Asp Gly Gly
            20                  25                  30

Leu Pro Thr Asn Tyr Ser Leu Thr Tyr Ser Lys Glu Gly Glu Lys Thr
        35                  40                  45

Thr Tyr Glu Cys Pro Asp Tyr Lys Thr Ser Gly Pro Asn Ser Cys Phe
    50                  55                  60

Phe Ser Lys Gln Tyr Thr Ser Ile Trp Lys Ile Tyr Ile Ile Thr Val
65                  70                  75                  80

Asn Ala Thr Asn Gln Met Gly Ser Ser Ser Asp Pro Leu Tyr Val
                85                  90                  95

Asp Val Thr Tyr Ile Val Glu Pro Glu Pro Pro Arg Asn Leu Thr Leu
            100                 105                 110

Glu Val Lys Gln Leu Lys Asp Lys Lys Thr Tyr Leu Trp Val Lys Trp
        115                 120                 125

Ser Pro Pro Thr Ile Thr Asp Val Lys Thr Gly Trp Phe Thr Met Glu
    130                 135                 140

Tyr Glu Ile Arg Leu Lys Pro Glu Glu Ala Glu Glu Trp Glu Ile His
145                 150                 155                 160

Phe Thr Gly His Gln Thr Gln Phe Lys Val Phe Asp Leu Tyr Pro Gly
                165                 170                 175

Gln Lys Tyr Leu Val Gln Thr Arg Cys Lys Pro Asp His Gly Tyr Trp
            180                 185                 190

Ser Arg Trp Ser Gln Glu Ser Ser Val Glu Met Pro Asn Asp Phe Thr
        195                 200                 205

Leu Lys Asp Thr Thr Val Trp Ile Ile Val Ala Ile Leu Ser Ala Val
    210                 215                 220

Ile Cys Leu Ile Met Val Trp Ala Val Ala Leu Lys Gly Tyr Ser Met
225                 230                 235                 240

Met Thr Cys Ile Phe Pro Pro Val Pro Gly Pro Lys Ile Lys Gly Phe
                245                 250                 255

Asp Thr His Leu Leu Glu Lys Gly Lys Ser Glu Glu Leu Leu Ser Ala
            260                 265                 270

Leu Gly Cys Gln Asp Phe Pro Pro Thr Ser Asp Cys Glu Asp Leu Leu
```

-continued

```
            275                 280                 285
Val Glu Phe Leu Glu Val Asp Asp Asn Glu Asp Glu Arg Leu Met Pro
    290                 295                 300

Ser His Ser Lys Glu Tyr Pro Gly Gln Gly Val Lys Pro Thr His Leu
305                 310                 315                 320

Asp Pro Asp Ser Asp Ser Gly His Gly Ser Tyr Asp Ser His Ser Leu
                325                 330                 335

Leu Ser Glu Lys Cys Glu Glu Pro Gln Ala Tyr Pro Pro Thr Leu His
                340                 345                 350

Ile Pro Glu Ile Thr Glu Lys Pro Glu Asn Pro Glu Ala Asn Ile Pro
                355                 360                 365

Pro Thr Val Asp Pro Gln Ser Thr Asn Pro Asn Phe His Val Asp Ala
    370                 375                 380

Pro Lys Ser Ser Thr Trp Pro Leu Leu Pro Gly Gln His Met Pro Arg
385                 390                 395                 400

Ser Pro Tyr His Ser Val Ala Asp Val Cys Lys Leu Ala Gly Ser Pro
                405                 410                 415

Val Asn Thr Leu Asp Ser Phe Leu Asp Lys Ala Glu Glu Asn Val Leu
                420                 425                 430

Lys Leu Ser Lys Ala Leu Glu Thr Gly Glu Glu Glu Val Ala Glu Gln
                435                 440                 445

Lys Gly Ala Lys Ser Phe Pro Ser Asp Lys Gln Asn Thr Pro Trp Pro
    450                 455                 460

Leu Leu Gln Glu Lys Ser Pro Thr Val Tyr Val Lys Pro Pro Asp Tyr
465                 470                 475                 480

Val Glu Ile His Lys Val Asn Lys Asp Gly Val Leu Ser Leu Phe Pro
                485                 490                 495

Lys Gln Arg Glu Asn Asn Gln Thr Glu Lys Pro Gly Val Pro Glu Thr
                500                 505                 510

Ser Lys Glu Tyr Ala Lys Val Ser Gly Ile Thr Asp Asn Asn Ile Leu
                515                 520                 525

Val Leu Val Pro Asp Ser Arg Ala Gln Asn Thr Ala Leu Leu Glu Glu
    530                 535                 540

Ser Ala Lys Lys Ala Pro Pro Ser Phe Glu Ala Asp Gln Ser Glu Lys
545                 550                 555                 560

Asp Leu Ala Ser Phe Thr Ala Thr Ser Ser Asn Arg Arg Leu Gln Leu
                565                 570                 575

Gly Arg Leu Asp Tyr Leu Asp Pro Thr Cys Phe Met His Ser Phe His
                580                 585                 590
```

USE OF A PROLACTIN RECEPTOR OR GROWTH HORMONE RECEPTOR INTRACYTOPLASMIC DOMAIN FOR ACHIEVING PROTEIN SECRETION

CROSS REFERENCES TO RELATED APPLICATIONS

This application is a 371 of PCT/FR96/01237 filed Aug. 2, 1996. This application further claims priority to French application 95/09420 filed Aug. 2, 1995.

BACKGROUND OF THE INVENTION

The invention relates to polypeptides which enable proteins which are produced in eukaryotic cells to be secreted directly.

In recent years, the baculovirus/insect cell system has been used successfully for expressing various genes of interest. In this system, as, in a more general manner, in the different systems which are known for producing recombinant proteins in host cells, it is desirable to have available means for exporting the said recombinant proteins into the medium in which the cells are cultured. This is because exporting these proteins makes it easier to harvest and purify them.

Generally, the approach is to attempt to use the standard secretion pathway, which involves the endoplasmic reticulum and the Golgi apparatus, in order to achieve the export of a recombinant protein from a eukaryotic host cell.

To this end, a cleavable N-terminal signal peptide is added to the protein which it is desired to have secreted by fusing a sequence encoding the said signal peptide to the sequence encoding the recombinant protein. The presence of this signal peptide enables the polypeptide to be translocated across the membrane of the endoplasmic reticulum, by way of which the polypeptide will be transported, in the vesicles of the Golgi apparatus, right up to the plasma membrane. However, this approach does not always enable the hoped-for result to be achieved [JARVIS et al., J. Biol. Chem. No. 268, pp. 16754–16762, (1993)].

The principal drawback of this strategy resides in the fact that passage by way of the endoplasmic reticulum and the Golgi apparatus can entail the addition, onto the polypeptide, of sugar residues which can result in the protein being folded incorrectly and/or in new epitopes being formed.

Moreover, it was observed, during the course of earlier work which was carried out by the inventors' group regarding expression of the prolactin receptor, or different portions of this receptor, in recombinant baculoviruses [CAHOREAU et al., Biochimie, No. 74, pp. 1053–1065, (1992)], that, when the intracytoplasmic region of the prolactin receptor was expressed on its own, it was excreted into the culture medium even though it did not possess any signal peptide.

Subsequent studies on the structure of this intracytoplasmic region showed that it was not N-glycosylated (even though it possesses several potential glycosylation sites) and that it was ubiquitinylated [CAHOREAU et al., FEBS Letters, No. 350, pp. 130–234, (1994)].

The prolactin (PRL) receptor belongs to a family of receptors (cytokine receptors) which also includes the receptors for growth hormone (GH) and those for several interleukins, those for erythropoietin and for GM-CSF (=granulocyte-macrophage colony stimulating factor) and the receptor for interferon γ, etc. These receptors consist of a N-terminal extracellular region, of a transmembrane region and of a C-terminal intracytoplasmic region (for review, see, for example [DUSANTER-FOURT et al., Médecine/Sciences Synthèse, 10, p. 825–835, (1994)]).

The prolactin receptor exists in two forms: a short form, which is composed of 291 amino acids, and a long form, which consists of 591 amino acids in the rat, 592 amino acids in the rabbit and 598 amino acids in man.

The growth hormone receptor consists of 620 amino acids (in man and rabbit) and exhibits a large number of regions which are homologous with the long form of the prolactin receptor [KELLY et al., in Recent Progress in Hormone Research, 48, p. 123 (Academic Press Ed. (1993); KELLY and DJIANE, U.S. Pat. No. 4,992,398]: in particular, 4 regions which are conserved are found in the intracytoplasmic region.

The other receptors of the same family (receptor for erythropoietin, receptors for growth factors, receptors for interleukins 2, 3, 4, 5, 6, 7, and 9, GM-CSF receptor, G-CSF receptor, receptor for interferon γ, etc.) also possess very closely related structures and the domains of different receptors can be combined with each other in order to produce functional chimeric receptors which comprise the extracytoplasmic domain of a first receptor and the intracytoplasmic domain of a second receptor, which domains are separated by a transmembrane domain belonging either to the first or to the second receptor [MOORE et al., FASEB J., 9 (6), A1414, (1995); CIOFFI et al., FASEB J., 7 (3–4), A430, (1993); DUSANTER et al., Journal of Cellular Biochemistry Supplement, 18B, p. 276, (1994)].

The inventors then showed that the intracytoplasmic region of the prolactin receptor was not only capable of being exported into the culture medium when it was expressed on its own, but was also capable of enabling a protein (termed "passenger" protein) to be exported when this protein was fused to its C-terminal end. The inventors additionally defined the minimum region which is responsible for this property.

Moreover, the inventors also observed that, when expressed in a baculovirus/insect cell system, the intracytoplasmic region of the growth hormone (GH) receptor was excreted into the culture medium in a manner which was analogous to that in which the intracytoplasmic region of the prolactin receptor was excreted. Thus, the inventors identified, in particular, a polypeptide of 372 amino acids which is encoded by the fragment of the sequence encoding the growth hormone receptor which is located between the NcoI site and the stop codon of the said sequence, and a polypeptide of 329 amino acids which is encoded by the fragment of the sequence encoding the growth hormone receptor which is located between the ClaI site and the stop codon of the said sequence.

The demonstration, by the inventors, of these characteristics of the receptors for prolactin and for growth hormone make it possible to envisage using the intracytoplasmic domains of cytokine receptors, and more specifically the intracytoplasmic domains of the receptors for prolactin and growth hormone, as transporters for enabling proteins of interest, whose localization is normally cytoplasmic or nuclear, to be exported from a host cell.

BRIEF SUMMARY OF THE INVENTION

The present invention relates to the use of a protein whose polypeptide sequence is selected from the group consisting of:

the sequence of the intracytoplasmic domain of the prolactin receptor, namely the region consisting of amino acids 235 to 591, in accordance with the numeration of the amino acids described by KELLY et al. (1993, loc. cit.), of the long form of the said receptor in the rat (SEQ ID NO:6) of amino acids 235 to 598 of the long form of the said receptor in man (SEQ ID NO:2), and of amino acids 235 to 592 of the long form of the said receptor in the rabbit (SEQ ID NO:4));

the sequence of the fragment of the prolactin receptor consisting of amino acids 240 to 592 of the long form of the said receptor in the rabbit (SEQ ID NO:4), of amino acids 235 to 591 of the long form of the said receptor in the rat (SEQ ID NO:6), and of amino acids 235 to 598 of the long form of the said receptor in man (SEQ ID NO:2);

the sequence of the intracytoplasmic domain of the growth hormone (GH) receptor, consisting, in man, of the C-terminal region, of 350 amino acids, of this receptor (SEQ ID NO:1);

the sequence of a fragment of the growth hormone (GH) receptor, comprising all or part of the intracytoplasmic domain of the said receptor, and comprising amino acids 271 to 620 of the said receptor in man (SEQ ID NO:1) (for example the fragment consisting of amino acids 249 to 620 (SEQ ID NO:1)), or else amino acids 272 to 620 of the said receptor in the rat (SEQ ID NO:5), or else amino acids 271 to 620 of the said receptor in the rabbit (SEQ ID NO:3), in order to achieve the secretion of a protein of interest which is produced in a eukaryotic host cell, in particular an insect host cell.

In order to implement the present invention, a eukaryotic cell expression system is caused to produce a chimeric fusion protein which comprises the protein of interest, which it is desired to export, which protein of interest is extended, at its N-terminal end, by the intracytoplasmic region of the prolactin receptor, or by the intracytoplasmic region of the growth hormone receptor, or by a fragment, as defined above, of one or other of these regions. Contrary to the chimeric receptors which are derived from cytokine receptors and which are described in the above-cited prior art, the chimeric proteins according to the invention do not include any transmembrane domain.

The two regions of the chimeric protein can either be fused directly or be separated by an oligopeptide which supplies a specific site for cleavage by a protease (for example a cleavage site for an enterokinase (EC 3.4.21.9), or for factor Xa (EC 3.4.21.6) or any other specific protease).

A chimeric protein according to the invention can be obtained by using the standard techniques of molecular biology to construct a recombinant gene which encodes this protein.

Such a recombinant gene comprises a DNA sequence encoding the protein of interest which it is desired to express, which sequence is fused, at its 5' end, to a sequence encoding the intracytoplasmic domain of the prolactin receptor or of the growth hormone receptor, or encoding a fragment, as defined above, of one or other of these domains; advantageously, these two sequences are separated by a sequence which encodes an oligopeptide which carries a specific site for cleavage by a protease.

Implementing the present invention makes it possible to recover the recombinant proteins from the culture medium, thereby facilitating their purification.

Furthermore, due to the fact that the export pathway represents an alternative to that which involves the endoplasmic reticulum and the Golgi apparatus, it has the advantage of enabling certain cytoplasmic or nuclear proteins, which do not require the post-translational modifications which are effected specifically in the endoplasmic reticulum and the Golgi apparatus, to be excreted into the culture medium in a soluble form.

The present invention also encompasses the vectors which at least carry a recombinant gene as defined above, and, in particular, expression vectors in which the said recombinant gene is placed under the control of sequences which regulate its expression and which are active in the chosen host cell. For example, if the said host cell is an insect cell, the said expression vectors can consist of modified baculoviruses in which at least one recombinant gene according to the invention is placed under the transcriptional control of a baculovirus promoter.

The present invention will be more clearly understood with the aid of the additional description which follows and which refers to examples of using the intracytoplasmic domain of the prolactin receptor to enable various proteins to be excreted.

It should nevertheless be understood, of course, that these examples are given solely by way of illustrating the subject-matter of the invention, to which they in no way constitute a limitation.

EXAMPLES

General Experimental Protocols

A—Cell and viral cultures

*Spodoptera frugiperda* Sf9 cells are maintained at 28° C. in TC100 medium which is supplemented with 5% foetal calf serum.

The baculovirus AcMNPV (wild-type virus), as well as the recombinant baculoviruses, are propagated in these Sf9 cells. For infection, the cells ($4 \times 10^6$ per 25 cm$^3$ flask) are inoculated with a viral suspension at a multiplicity of infection of 10 PFU per cell. After adsorbing for an hour at room temperature, the viral inoculum is removed and fresh culture medium is added.

The recombinant viruses are obtained after using lipofection (DOTAP, Boehringer Mannheim, Germany) to co-transfect the Sf9 cells with the viral DNA and the DNA of the transfer vector [FELGNER and RINGOLD, Nature No. 337, pp. 387–388, (1989)]. The recombinant viruses are screened and purified using the standard procedures which are described, for example, by SUMMERS and SMITH [Texas Agric. Exp. St. Bull., No. 1555, pp. 1–56, (1987)].

Figure 1:
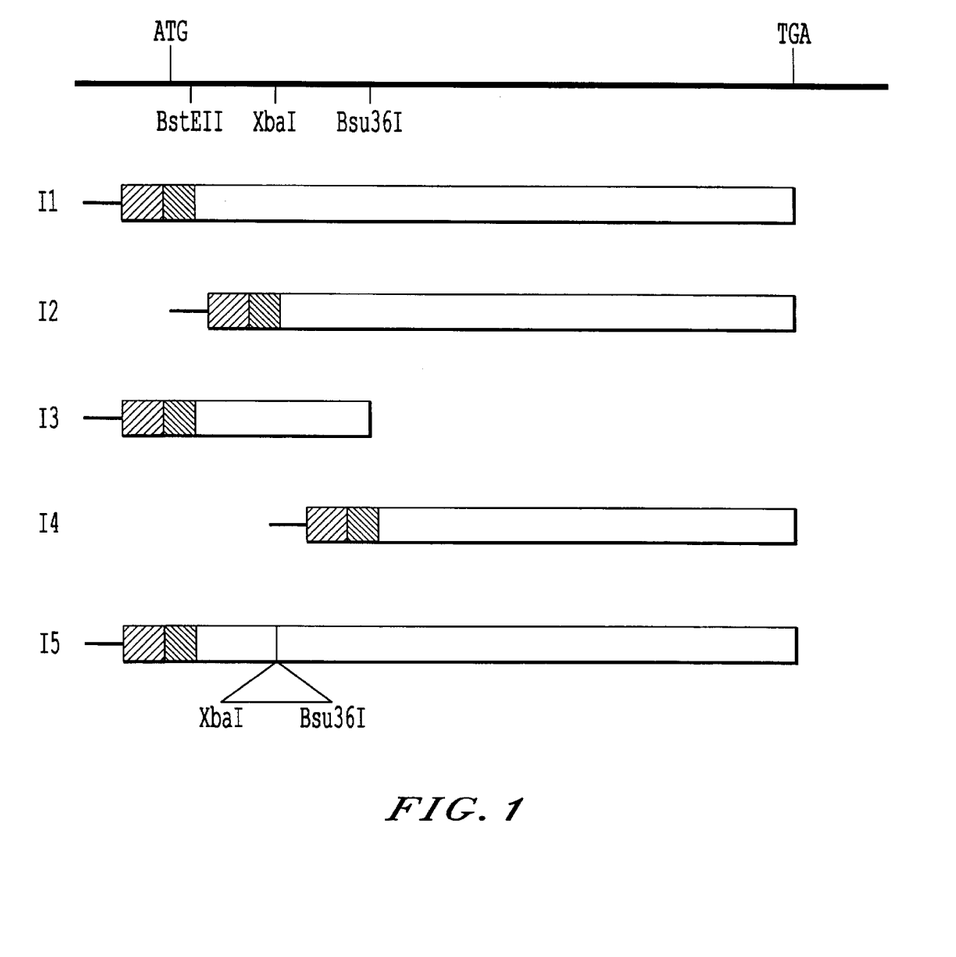
FIG. 1: The long form of the rabbit prolactin receptor. Shown are the relative positions of the start (ATG); stop (TGA) codons, and several restriction enzyme cleavage sites. Fragments I1 to I5 corresponding to the parts of the prolactin receptor inserted into baculovirus transfer vectors.

B—Cloning the sequence which encodes the intracytoplasmic region of the long form of the rabbit prolactin receptor The long form of the rabbit prolactin receptor consists of an N-terminal extracellular domain of 210 amino acids, a transmembrane region of 24 amino acids and a C-terminal intracytoplasmic region of 358 amino acids (FIG. 1). Several restriction enzyme cleavage sites are present in the gene which encodes the rabbit prolactin receptor [EDERY et al., Proc. Natl. Acad. Sci. USA, No. 86, 2112–2116 (1989)].

The 5 kb cDNA sequence which encodes the rabbit prolactin receptor was cloned from plasmid pECE-PRL- R₂4, which is described by EDERY et al., (1989, loc. cit.), into a pUC18 plasmid in order to produce the plasmid pUC18 L2 PRL-R [CAHOREAU et al., Biochimie, No. 74, pp. 1053–1065, (1992)].

C—Transfer plasmids

The baculovirus transfer plasmids of the pGmAc family are prepared from the EcoRI-I fragment of the *Autographa californica* nuclear polyhedrosis baculovirus (AcMNPV), which contains the polyhedrin gene and promoter, by inserting the said fragment into the bacterial plasmid pUC8.

In order to obtain the plasmid pGmAc31, the coding sequence situated between nucleotides +24 and +522 (in relation to the A(+1) of the ATG of the polyhedrin gene was deleted and replaced with a SmaI linker, thereby enabling a heterologous sequence to be inserted in frame downstream of the ATG of the polyhedrin. The recombinant protein is thus produced in the form of a fusion protein together with the first 7 amino acids of the polyhedrin. In addition, this plasmid possesses a KpnI restriction site which is located 109 nucleotides downstream of the SmaI site.

Example 1

Effect of Different Deletions on Secretion of the Intracytoplasmic Domain of the Prolactin Receptor In order to identify the minimum sequence responsible for the secretion, various regions of the intracytoplasmic domain were expressed in insect cells.

The plasmids pGmAc31I$_1$, pGmAc31I$_2$, and the recombinant baculoviruses which express these plasmids, are obtained as described in the publication by CAHOREAU et al. [CAHOREAU et al., Biochimie, No. 74, pp. 1053–1065, 1992]. pGmAc31I$_1$ results from inserting a 1151 bp BstEII/KpnI fragment, which encompasses the whole of the sequence encoding the intracytoplasmic part of the prolactin receptor, between the SmaI site and the KpnI site of pGmAc31, and contains a sequence which encodes 353 C-terminal amino acids of the prolactin receptor. pGmAc31I$_2$ results from inserting a 998 bp SmaI/KpnI fragment between the SmaI site and the KpnI site of pGmAc31 and contains a sequence which encodes 302 C-terminal amino acids of I$_1$.

Three truncated forms were constructed, with these truncated forms being obtained by internal (I5), N-terminal (I4) or C-terminal (I3) deletions of the I$_1$ fragment:

pGmAc31I$_3$:

This plasmid contains the BstEII/Bsu36I sub-fragment of the I$_1$ fragment. This subfragment encodes 114 N-terminal amino acids of I$_1$.

pGmAc168I$_4$:

The plasmid pGmAc31I$_2$ was cleaved with Bsu36I, provided with blunt ends using KLENOW polymerase, and cut with Asp718. The 729 bp DNA fragment which results from this was ligated into the pGmAc168 transfer vector, which was cleaved between BglII (end repaired with KLENOW polymerase) and Asp718. (The pGmAc168 transfer vector contains a deletion of the polyhedrin gene between nucleotides +5 and +483 (in relation to the A of the ATG). A BglII linker was inserted between these two positions). The insertion of the I$_4$ fragment in frame with the first 5 nucleotides of the polyhedrin results in the production of a fusion protein which includes 1 additional amino acid derived from the polyhedrin. The resulting plasmid is designated pGmAc168I$_4$. It contains a subfragment which encodes 239 C-terminal amino acids of I$_1$.

pGmAc31I$_5$:

In order to obtain this plasmid, pGmAc31I$_1$ was digested with XbaI and Bsu36I; an XbaI/Bsu36I fragment was deleted; both ends of this fragment were rendered blunt using KLENOW polymerase and ligated to a BamHI linker (10 mer). The plasmid which was obtained contains a subfragment which encodes 52 N-terminal amino acids of I$_1$, fused to a subfragment which encodes 239 C-terminal amino acids of I$_1$.

The inserts I$_1$, I$_2$, I$_3$, I$_4$ and I$_5$, located with respect to the sequence encoding the intracytoplasmic domain of prolactin, are depicted in FIG. 1 by plain white rectangles. The polyhedrin promoter is depicted in plain black; the beginning of the sequence encoding the polyhedrin is depicted by black dots on a white background.

Three recombinant baculoviruses, designated AcPhI$_3$, AcPhI$_4$ and AcPhI$_5$ were obtained by means of homologous recombination between pGmAc31I$_3$, pGMAc168I$_4$ and pGmAc31I$_5$, respectively, and the total DNA of wild-type AcMNPV. A recombinant baculovirus which expressed the protein I$_2$ was used as a positive control.

*Spodoptera frugiperda* cells were infected with each of these viruses. 48 h after the infection, the cell lysates and the culture media were analysed following immunoelectrophoretic transfer to a nitrocellulose membrane and visualization using an anti-prolactin receptor polyclonal serum as described by CAHOREAU et al. [Biochimie, No. 74, pp. 1053–1065, 1992].

The results obtained indicate that the three proteins, I$_3$, I$_4$ and I$_5$, retain the capacity to be secreted into the cell culture medium.

Example 2

Use of the Intracytoplasmic Domain of the Prolactin Receptor, or of its Fragments, for Enabling Cyclin B and Cyclin A to be Secreted In order to study the ability of the different fragments of the intracellular domain of the prolactin receptor to transport a passenger protein, recombinant baculoviruses were constructed which expressed these fragments fused, by their C-terminal end, to the N-terminal end of a passenger protein. Cyclin A or cyclin B were used as the passenger proteins.

Cyclin A and cyclin B have already been expressed in the baculovirus/insect cell system. Under these conditions, cyclin A is present in the nucleus of the infected cells [ZINDY, F., "Etude des fonctions et de l'expression de la cycline A humaine normale et de sa forme modifiée par l'integration de l'ADN du virus de l'hépatite B" [Study of the functions and of the expression of normal human cyclin A and of its form which is modified by integration of the DNA of hepatitis B virus], Thesis, Université Paris 6, Jun. 15, 1993], whereas cyclin B forms insoluble granules in the cytoplasm of the cells [LORCA et al., Mol. Cel. Biol. 11, pp. 1171–1175, (1991)]; these are therefore proteins which are not normally excreted.

The transfer vector pGmAc31I$_2$ was modified by mutation of the stop codon (TGA) of the intracytoplasmic domain of the prolactin receptor, such that it is replaced by a KpnI site. The KpnI/KpnI fragment is then deleted by digestion with the restriction enzyme KpnI, after which the vector is religated.

Figure 2:
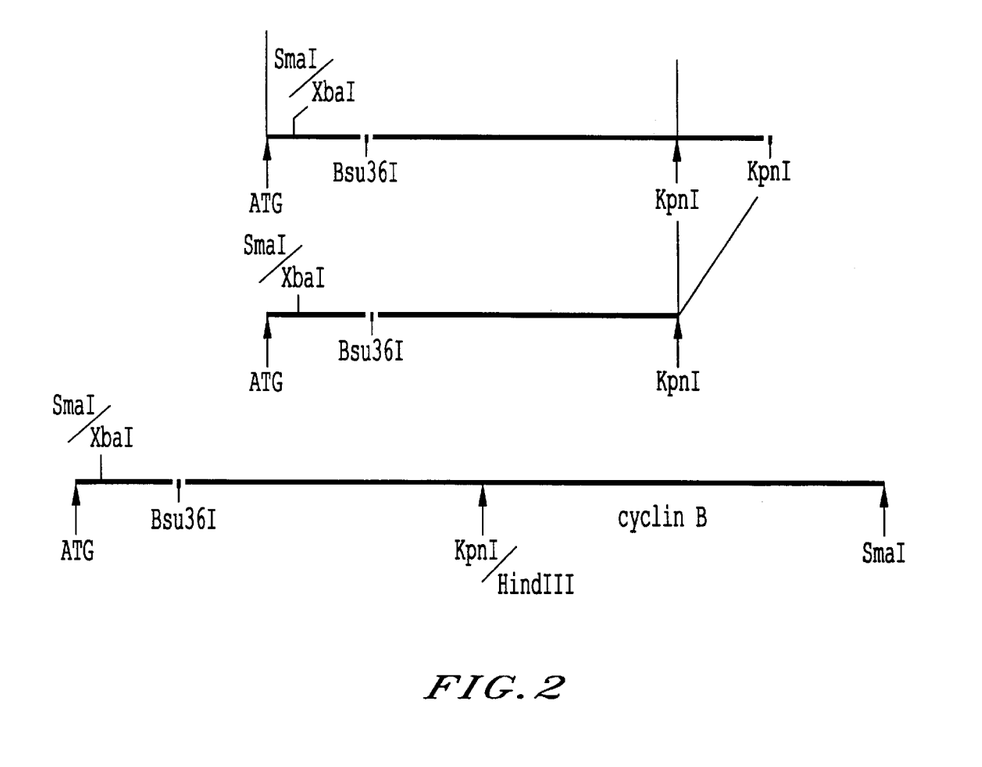
FIG. 2: The steps involved in the construction of cyclin A and cyclin B into the transfer vector pGmAc31I$_2$.

The two cDNAs encoding cyclin A and cyclin B, respectively, were inserted into the remaining unique KpnI site: the gene for cyclin B was cut with HindIII, repaired with KLENOW enzyme and SmaI and then inserted into the KpnI site, which had been repaired with KLENOW enzyme, of the transfer vector. The different steps in this construction are illustrated by FIG. 2.

The complete sequence of the gene encoding cyclin B was inserted into the BglII site, which had been repaired with KLENOW enzyme, of the transfer vector pGmAc31I$_3$. In the case of cyclin A, the ATG of the gene was replaced such that a KpnI site is obtained, and a KpnI/KpnI fragment encompassing the entire cyclin A gene was inserted directly into the KpnI site of the transfer vector.

The CycB gene was thus inserted into the pGmAc31I$_2$ and pGmAc31I$_3$ transfer vectors while the CycA gene was inserted into pGmAc31I$_2$. The recombinant viruses, designated AcPhI$_2$-CycB, AcPhI$_3$-CycB and AcPhI$_2$-CycA, respectively, were obtained by means of homologous recombination between these transfer vectors and the total DNA of wild-type AcMNPV.

Baculoviruses which only expressed the sequences encoding cyclin A and cyclin B, which sequences were not fused to the intracytoplasmic domain of the prolactin receptor, were also constructed as controls.

*Spodoptera frugiperda* cells were infected with each of the recombinant viruses over a period of 48 hours and the proteins of the cell extracts and of the culture supernatants were characterized by immunoelectrotransfer using an anti-prolactin receptor polyclonal antiserum.

The results are as follows:

Cyclin A and cyclin B on their own were only detected in the cell lysates; no secretion into the culture medium can be detected.

The chimeric proteins I$_2$-CycB and I$_2$-CycA are present both in the cell lysates and in the cell culture media. Each of the proteins fused to I$_2$ is therefore secreted effectively.

The chimeric protein I$_3$-CycB accumulates in the cytoplasm, indicating that deletion of the C-terminal portion of the I$_2$ domain substantially decreases secretion efficiency.

The immunodetection using an anti-ubiquitin antiserum demonstrates that while I$_2$CycB and I$_2$CycA are ubiquitinylated, CycA, CycB and I$_3$CycB are not. It is therefore possible that the ubiquitin residues play a role in the secretion process.

What is claimed is:

1. A chimeric protein comprising: a first region containing a protein of interest that is desired to be exported, wherein said protein of interest is extended at the amino-terminal end with a second region wherein said second region consists of an amino acid sequence selected from the group consisting of amino acids 240 to 592 of SEQ ID NO:4, amino acids 235 to 591 of SEQ ID NO:6, amino acids 235 to 598 of SEQ ID NO:2, amino acids 271 to 620 of SEQ ID NO:1, amino acids 272 to 620 of SEQ ID NO:5, and amino acids 271–620 if SEQ ID NO:3.

2. The chimeric protein according to claim 1, wherein the two regions are separated by an oligopeptide comprising a specific site for cleavage by a protease.

3. A method of secreting a protein of interest from a cell comprising extending the amino-terminal end of said expressed protein with a second region, wherein said second region consists of an amino acid sequence selected from the group consisting of amino acids 240 to 592 of SEQ ID NO:4, amino acids 235 to 591 of SEQ ID NO:6, amino acids 235 to 598 of SEQ ID NO:2, amino acids 271 to 620 of SEQ ID NO:1, amino acids 272 to 620 of SEQ ID NO:5, and amino acids 271–620 of SEQ ID NO:3; and expressing said extended protein in a cell.

4. The method of claim 3, wherein the two regions are separated by an oligopeptide comprising a specific site for cleavage by a protease.

5. The method of claim 3 wherein after the expressing, the method further comprises collecting the secreted protein, and cleaving the protein with a protease.

6. A polynucleotide encoding the chimeric protein of claim 2.

7. A polynucleotide encoding the chimeric protein of claim 1.

8. A vector containing the polynucleotide of claim 6.

9. A vector containing the polynucleotide of claim 7.

10. A eukaryotic cell comprising the polynucleotide of claim 6.

11. A prokaryotic cell comprising the polynucleotide of claim 6.

12. A eukaryotic cell comprising the polynucleotide of claim 7.

13. A prokaryotic cell comprising the polynucleotide of claim 7.

* * * * *